United States Patent [19]

Cattani

[11] 4,386,910
[45] Jun. 7, 1983

[54] CONSOLE FOR SUCTION TUBES OF SUCTION UNITS USED IN DENTISTRY

[75] Inventor: Augusto Cattani, Parma, Italy

[73] Assignee: Officine Augusto Cattani & C.S.a.S., Parma, Italy

[21] Appl. No.: 249,234

[22] Filed: Mar. 30, 1981

[30] Foreign Application Priority Data

May 2, 1980 [IT] Italy ............................... 28946/80[U]
Aug. 29, 1980 [IT] Italy ............................... 28992/80[U]

[51] Int. Cl.³ ........................................... A61C 17/04
[52] U.S. Cl. ..................................... 433/92; 210/452; 433/28; 433/79
[58] Field of Search .......................... 433/92, 28, 79; 210/465, 469, 477, 406, 452, 470, 471; 128/276, 278; 251/331

[56] References Cited

U.S. PATENT DOCUMENTS

| | | | |
|---|---|---|---|
| 3,422,850 | 1/1969 | Caldwell | 251/331 |
| 3,484,941 | 12/1969 | Svard | 433/92 |
| 3,502,220 | 3/1970 | Kohlberg | 210/452 |
| 3,636,974 | 1/1972 | Beguiristain | 433/92 |
| 3,657,819 | 4/1972 | Soderqvist | 433/92 |
| 3,748,837 | 7/1973 | Billeter | 210/452 |
| 3,847,573 | 11/1974 | Gandrud | 433/92 |
| 4,226,590 | 10/1980 | Hofmann | 433/28 |

FOREIGN PATENT DOCUMENTS 13667 7/1980 European Pat. Off. .............. 433/92
1466999 4/1969 Fed. Rep. of Germany ........ 433/79

Primary Examiner—Gene Mancene
Assistant Examiner—John J. Wilson
Attorney, Agent, or Firm—Browdy and Neimark

[57] ABSTRACT

The invention concerns a console specifically designed for the suction tubes of suction units used in dentistry.

The console basically comprises a box-like shell which is furnished with a collector, maintained in a state of vacuum and connected to the suction tubes, inside of which is a filter drawer through which pass all the fluids sucked in by the tubes. There is a compartment located in the top of the box-like shell, its top open, which contains the pneumatic and electrical command devices necessary to the console's functioning.

The console further comprises a cover in which are located the forked housings for the tubes, which can be attached directly to the top of the box-like shell or which can be connected to the box-like shell by means of articulating arms which allow adjustment of the position of the cover and, consequently, the tubes' housings, with respect to the box-like shell, which will normally be fixed to the dentist's main assembly.

9 Claims, 7 Drawing Figures

CONSOLE FOR SUCTION TUBES OF SUCTION UNITS USED IN DENTISTRY

BACKGROUND OF THE INVENTION

The invention herein described is a console specifically designed for the suction tubes of suction units used in dentistry. These suction units for dental use are provided with suction tubes which are used for the extraction of blood, saliva, rinsing water and other foreign bodies which accumulate in the patient's mouth during the course of a session of treatment.

When not in use these tubes are placed in housings, usually fork-shaped, varying in number according to the number of tubes and located on a console to which the tubes are usually attached by means of a flexible hose through which is created at the mouth of the tube the vacuum necessary to inducing suction.

Also connected to the console by means of a further hose are the means whereby a vacuum is produced, these normally being suction pumps of one kind or another.

There is normally some provision made in the console for means whereby the suction within a tube may be arrested when the latter is replaced on the actual console, means for arresting the operation of the pump when all the tubes are replaced on the console, and means for effecting a first stage filtering of the spittle withdrawn from the patient's mouth by the tube.

To be able to perform these functions the consoles above-mentioned need to be of somewhat large dimensions, this factor often being a source of difficulty in that the available space surrounding the operator's work area is often restricted, and they present a rather complex character, a factor which brings with it difficulties and above all, increased production costs.

Such consoles are usually fixed to the dentist's main assembly so that it may happen, during the course of treatment, the dentist finds himself in such a position that only with difficulty can he replace the tube on, or withdraw it from the console.

The object of the invention herein described is to eliminate the above-mentioned inconveniences by providing a console of considerably reduced dimensions, which is simple and inexpensive to produce.

A further object of the invention herein described is to provide a console in which cleaning and maintenance operations are rendered extremely simple both the frequent ones such as the removal and cleaning of the filter, or the occasional ones, for example, cleaning or replacement, in case of breakdown, of pneumatic or electrical parts.

A further object of the invention herein described is to provide a console which allows the dentist to replace the tube on, or withdraw it from the console comfortably, no matter what position he happens to find himself in.

SUMMARY OF THE INVENTION

These and other objects too have all been attained with the console herein described of a type having one or more housing(s) for the tube(s) and comprising pneumatic devices for arresting the suction within a tube when the latter is replaced on the console itself, electrical means for arresting the operation of the suction pump when all the tubes are replaced on the console, filtering means for effecting a first stage filtering of the spittle extracted by the tube, characterised by the fact that it comprises: a box-like shell furnished internally with a longitudinally disposed collector, accessible from without through one of its lateral extremities and closed by a removable stopper, inside of which is positioned a filter drawer with an open top and perforated walls whose shape and dimensions are such that it occupies almost all the collector's internal space. The collector is connected to the suction pump by a first hose and, by the interpositioning of a pneumatic valve, to each of the tubes by means of second hoses, which second hoses are connected to a duct located in the box-like shell which goes out into the collector and, correspondingly into the top of the filter drawer. The box-like shell also an furnished with an upper compartment with open top which serves to accomodate the pneumatic devices and the command components of the electrical devices; a cover in which are located the forked housings into which the tubes are placed can be attached to the top of the said box-like shell, thereby making it secure.

BRIEF DESCRIPTION OF THE DRAWINGS

Further characteristics and advantages of the present invention will emerge more clearly from the detailed description that follows of a preferred but not exclusive form of embodiment for the console herein described illustrated purely as an unlimited example on the accompanying drawings.

DESCRIPTION OF THE PREFERRED EMBODIMENTS

Figure 1:
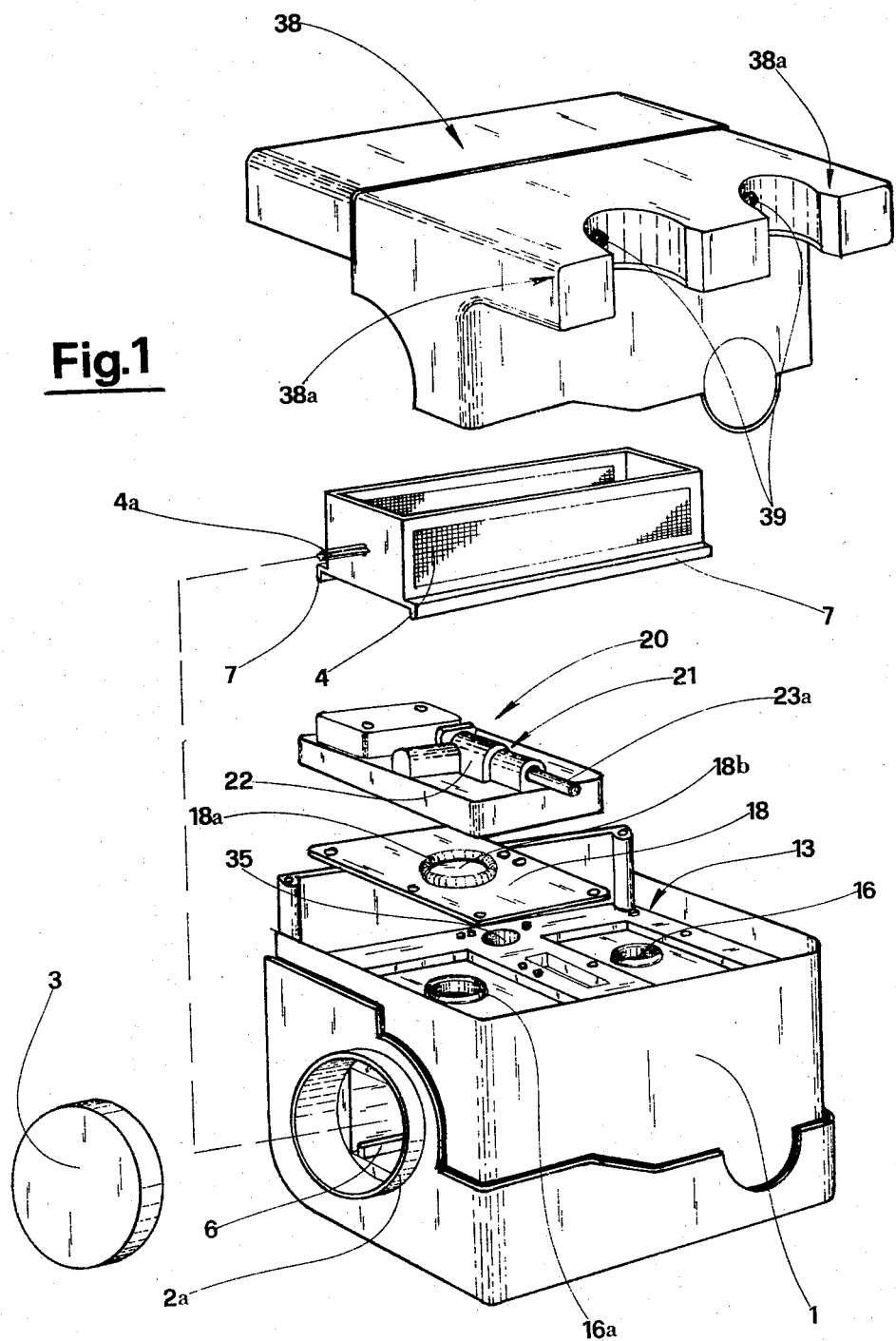
FIG. 1 prospective layout view of a first form of embodiment of the console herein described.
Figure 3:
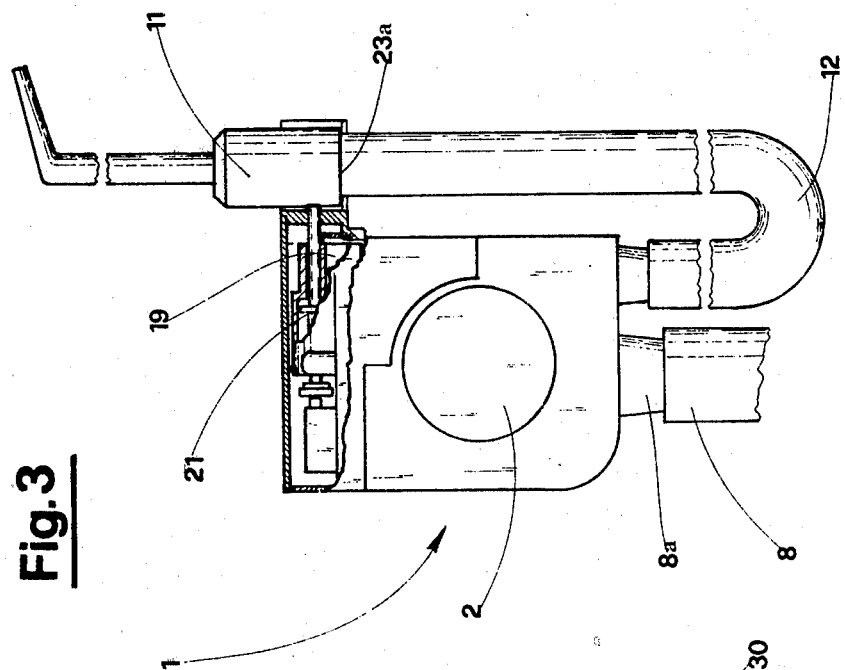
FIG. 3 shows a vertical elevation of the side view of the first embodiment of the console herein described with certain parts cut away to better reveal others.
Figure 2:
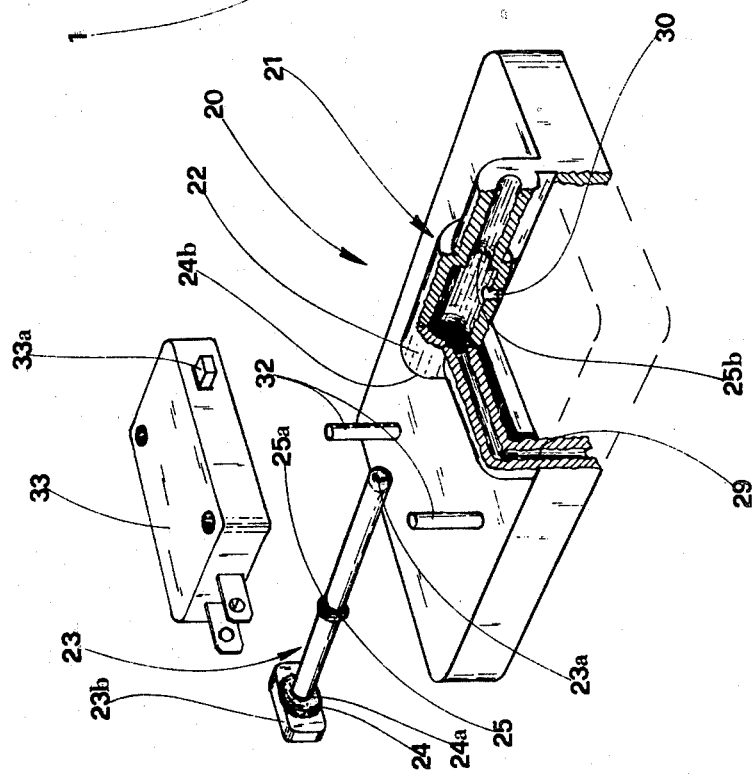
FIG. 2 prospective view, with certain parts cut away to better to reveal others, of a particular covering which forms part of a first embodiment of the console herein described.
Figure 4:
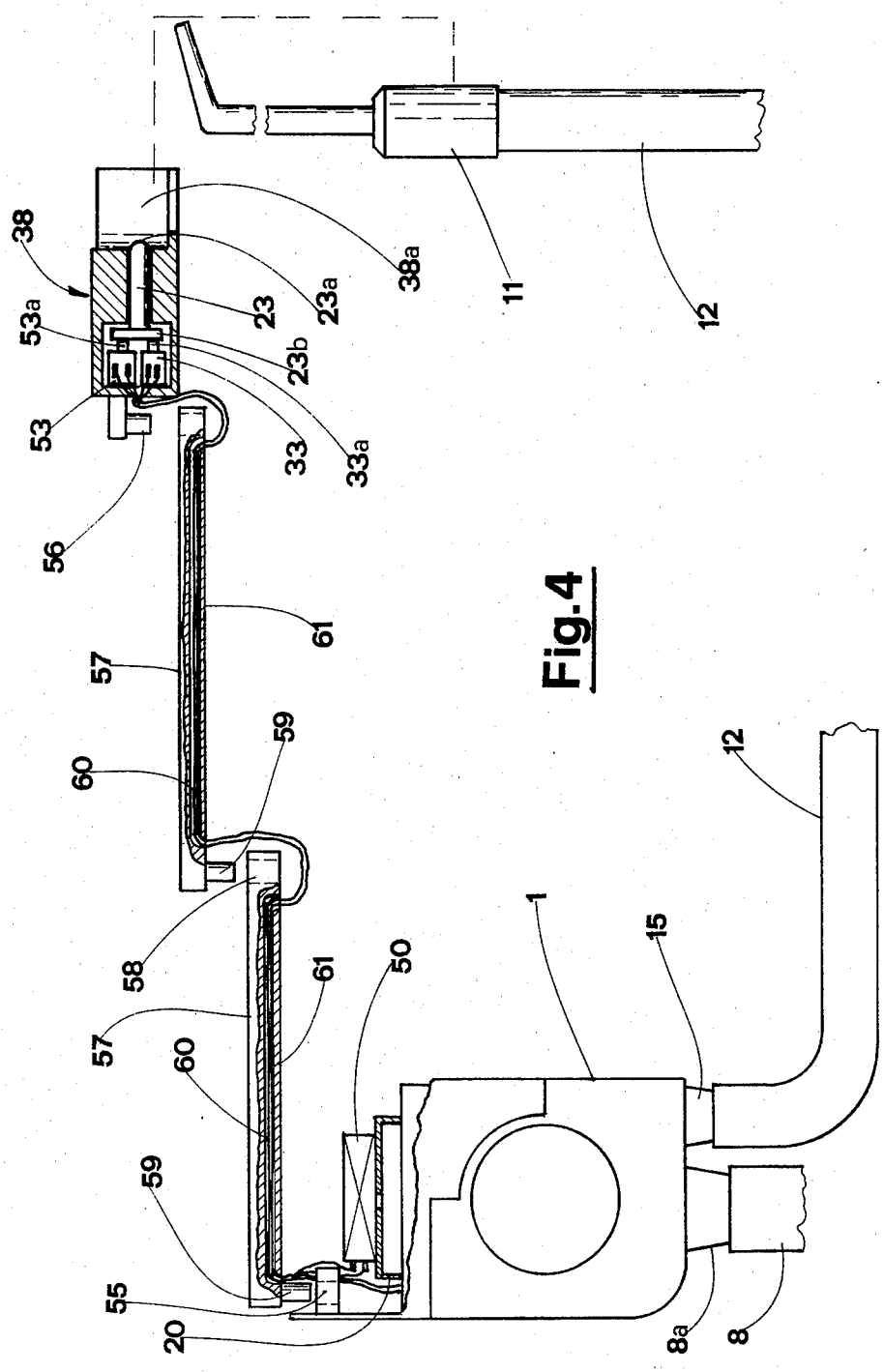
FIG. 4 shows a vertical elevation of the side view of the console herein described with certain parts cut away to better reveal others.
Figure 5:
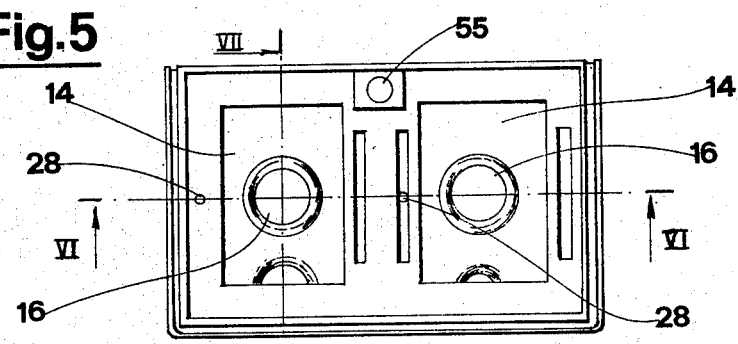
FIG. 5 shows a view from above of the box-like shell of the console herein described.
Figure 6:
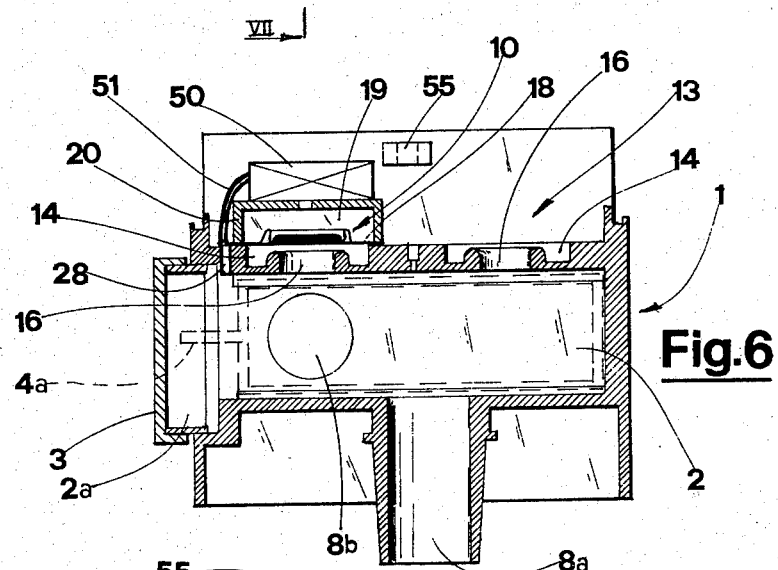
FIG. 6 shows a cross-section of the box-like shell as seen on line VI—VI in FIG. 5 and certain particulars of the second embodiment of the console herein described.

The console herein described whereof the attached drawings show a design intended to hold two suction tubes comprises a box-like shell (1) of basically parallelepiped form furnished with an internal collector (2) which is rectangular in cross-section and longitudinally disposed, accessible from without through one of the lateral extremities (2a), and closed by a removable stopper (3), being screwed to the extremity itself and furnished with a washer that ensures its being sealed tight. The upper part of the body has a compartment, open at the top, which serves to accomodate pneumatic devices for arresting suction within a tube when the latter is replaced on the console, and the command components of the electrical devices which arrest the suction pump when all the tubes are replaced on the console.

Inside the compartment (3), to be precise on the bottom side of same, there is located a cavity (14) for each tube respectively, each parallelepiped in form, open at the top, and which will be more fully illustrated in the following.

Inside the collector (2) there is positioned a filter drawer (4), parallelepiped in form and of dimensions such that it occupies almost all the collector's internal space. The lateral plane of the filter uppermost is open while the other lateral planes are perforated; the outward-facing base of the filter drawer is furnished with a handle (4a), which makes it possible to grasp the drawer from without and to introduce it into, or withdraw it from the collector.

In order to determine the exact position of the filter for its introduction into the collector and to ensure that the open plane of the filter always faces upwards, provision is made for checking devices which comprise two pairs of guide rails, upper rails (5) and lower rails (6), located on the internal upper surface and on the internal lower surface respectively of the collector (2), running longitudinally and parallel with each other. The distance between the upper pair of guide rails is slightly greater than the width of the open plane of the filter whilst the distance between the lower pair of guide rails is less than that said width; furthermore, the distance between the guide rails upper (5), and lower (6) is less than the width of the open plane of the filter.

On the lower plane of the filter, in other words that plane opposite to the open plane, provision is made for a pair of corresponding elements (7) running longitudinally and inclined downwards, parallel with each other at a reciprocal distance slightly greater than that distance existing between the outer surfaces of the lower pair of guide rails (6). When the filter is introduced into the collector its corresponding elements (7) slide externally in relation to the guide rails (6), while the open plane of the filter runs internally in relation to its guide rails (5).

In any position other than that described the width of the open plane and the disposition of, and distance between the guide rails are such that they do not allow the filter's introduction into the collector:

Consequently, there is only one position which allows the filter to be introduced into the collector (2), it being that wherein the open plane of the filter faces upwards.

The collector (2) is connected to a suction pump (not shown in the drawing) by means of a first flexible hose (8) one of whose extremities is connected to a first manifold (8a) located on the box-like shell (1) which gives out into the collector (2). In the event that it is wished to connect the hose (8) to the rear part of the box-like shell (1) rather than to the underside, there is provision made in the rear part of the said box-like shell (1) for a second manifold (8b). The aperture not being used for connection of the hose (8), the second aperture in the case illustrated here (8b), is hermetically sealed with a plug.

The collector (2) is also connected, by the interpositioning of a pneumatic valve about which more will be said later, to each of the suction tubes (11); connection to each of the individual tubes is achieved by means of a second flexible hose (12), one of whose extremities is connected to the tube itself and whose other extremity is connected to a duct located in the box-like shell which gives out into the collector through the open plane of the filter drawer.

Each duct comprises a first conduit (15) located within the box-like shell (1) one of whose extremities gives out into the bottom of the cavity (14) aforementioned; to the other extremity of the conduit (15) is connected the second hose (12). Each duct further comprises a through hole (16) located in the bottom of the cavity (14) and positioned in direct communication with the collector (2); one of the hole's (16) extremities (16a) gives out into the cavity (14) at a height superior in respect of the level of the bottom of the cavity (14) but inferior with respect to the rim of the cavity itself.

Positioned above each cavity (14) is a diaphragm (18) whose dimensions are such that it completely covers the cavity, which constitutes the choke of the pneumatic valve (10).

The diaphragm (18) presents a convex aspect (18a) to the hole (16) when its perimeter is seated, its inner area defining a sealing surface (18b) when the valve is in closed position completely covering the hole's aperture (16). The sealing surface (18b) is of a thickness greater than that of the remaining area of the diaphragm (18). The rim which defines the hole's (16) extremity (16a) constitutes the seat of the pneumatic valve (10). The console herein described further comprises a covering element (20) for each respective cavity whose outer perimeter completely surmounts the diaphragm (18) and, therefore, the cavity (14).

This element (20) is attached to the box-like shell (1) by means of screws and creates a chamber (19) above the diaphragm (18). In the first embodiment of the console, on the element's upper side there is positioned the body (22) of a shut-off valve (21) furnished with a sliding shaft (23) running through the body of the valve and protruding from both extremities of same, foremost (23a) and hindmost (23b) respectively.

On special grooves (24a) and (25a) in the shaft (23) are located sealing elements (24) and (25) which allow the opening and shutting of the valve (21) by resting against or by being spaced from sealing rings (24b) and (25b) positioned on the hindmost part of the body (22) and on its inner area, respectively.

The valve thus offers two points of entry.

The chamber (19) created by the element (20) communicates with the collector (2) by way of a second conduit whose first part consists of a through hole (28) located in the box-like shell (1), and connects the collector to the bottom side of the compartment (13), and whose second part is located in the covering element (20), and constitutes an internal channel (29) within the body of the valve (22) and a small hole (30) which connects the interior of the body of the valve (22) to the chamber (19). A sealed connection between the first and second parts of the second conduit is assured by a hole located in the diaphragm (18). The small hole (30) further allows that, when the shaft is moved into the position which opens the shut-off valve (21), and this happens when the relative tube is replaced on the console, the chamber (19) may communicate with the outside atmosphere.

For reasons which will become clear during the description of the console's function, the bore of the second conduit is greatly reduced and hence noticeably less than that of the outward facing apertures of the shut-off valve (21), thereby producing a marked drop in pressure at its heads when the interior of the valve (21) is placed in communication with the outside, that is to say, with atmospheric pressure.

On the upper side of each covering element (20) are attached supporting posts (32) which serve to accomodate a switch (33) that constitutes the command component for the said electrical devices. The posts (32) are placed in close proximity to the rear extremity (23b) of the shaft (23) in order that the extremity (23b) itself, being appropriately enlarged, may effect the command by pressing the switch's (33) button (33a) which is furnished with a return spring, when the tube is replaced on the console.

There is a through hole (35) located in the bottom of the compartment (13) which allows the passage of wires coming from the switches (33). The switches (33) are wired so that the operation of the suction pump is arrested when all the tubes are replaced on the console. In the event of more than one console being connected to the same pump the switches will break by means of a solenoid valve—not shown in the drawing—arresting suction relative to the particular console.

On each covering element in the second embodiment of the console there is fixed a second, solenoid valve (50) with two points of entry, whose outlet is likewise connected to the chamber (19); one of the solenoid valve's (50) points of entry communicates with the outside, whilst the second point of entry communicates, by way of a second conduit, with the collector (2). The said second conduit comprises a first part, consisting of a through hole (28) located in the box-like shell (1) which connects the collector with the bottom of the compartment (13), and a second part consisting of a small bore flexible hose (51) which connects the hole (28) to one of the solenoid valve's points of entry. The solenoid valve (50) thus causes the chamber (19) to communicate with the outside, and with the collector, (2) alternately.

The console further comprises a cover (38) on which are located the forked housings (38a) which accomodate the replaced tubes (11). In the first embodiment of the console this cover may be attached, for example by means of screws, onto the box-like shell thereby making it secure and enclosing the compartment.

At a point corresponding to the center of each of the forked housings (38a) provision is made for a through hole (39) which allows the foremost extremity of the shaft (23a-23) to protrude from the cover.

In the second embodiment of the console, inside the cover (38), in relation to each of the tubes there is housed, in addition to the electrical switch (33), a second electrical switch (53). There is positioned in the cover (38), in relation to each tube respectively, a sliding shaft (23) one of whose extremities (23a) protrudes through the hole from the cover at a point corresponding to the center of the forked housing (38a) whilst the enlarged hindmost extremity (23b) is positioned correspondingly adjacent to the buttons (33a) and (53a) of the respective switches (33 and 53), engaging them when the tube is replaced in the forked housing (38a).

In the said embodiment the shaft (23) has the sole function of commanding the electrical switches (33 and 53).

The electrical switches (33) perform the same functions in either embodiment.

Each one of the switches (53) is wired to its respective solenoid valve (50), whose function will be described below.

In the second embodiment of the console provision is made for the attachment of the cover (38) to the box-like shell (1) by means of articulated joints comprising: a first socket (55) incorporated into the box-like shell, a first pin (56) incorporated into the cover; the means further comprise at least one arm (57) which is furnished at one of its extremities with a second socket (58) whose dimensions are such that it may receive the first pin (56) and at the other of its extremities with a second pin (59) whose dimensions are such that it may be inserted into the first socket (55). By inserting the pin incorporated in the arm into the socket (55) incorporated into the box-like shell, and the pin (56) incorporated in the cover into the socket (58) incorporated into the arm one achieves connection of the cover to the box-like shell in such a way as to permit the cover itself to deviate with respect to the box-like shell and thus to follow the dentist's movements as he adopts varying different postures. Normally, in place of the single arm (57) a number of arms would be used, connected in such a way as to enable the insertion of the pin of one into the socket of the next, thus allowing an increased freedom of movement for the cover (38).

The underside of each of the arms (57) offers a longitudinal groove (60) enclosed, save at its extremities, by a covering element (61). By this means it is possible to thread through the said groove those wires coming from the cover which go to either the box-like shell or to the first solenoid valves, without their hindering the cover's movement.

In the first embodiment, when both tubes are withdrawn from the console the suction pump is in operation thus causing a vacuum to be created in the collector (2) and, therefore, on the underside of the diaphragm (18); the return springs in the buttons (33a) push forward the shafts (23) occasioning closure of the ways of access to the interior of the shut-off valves (21).

Figure 7:
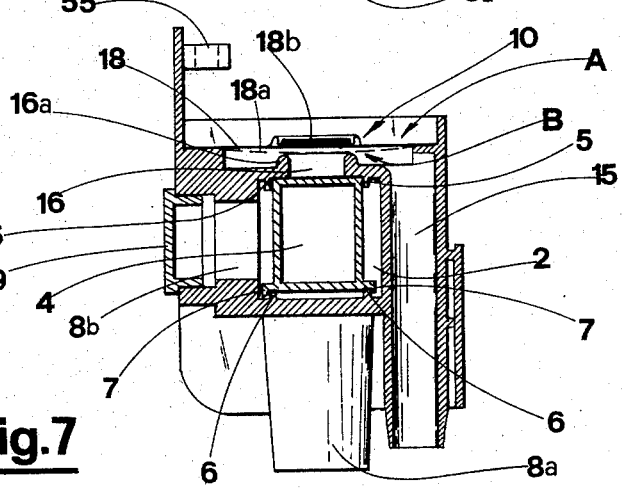
FIG. 7 shows a cross-section of the box-like shell of both embodiments of the console herein described as seen on line VII—VII in FIG. 5.

Each chamber (19) that communicates with the collector (2) is thus maintained in a state of vacuum; in this way each diaphragm (18), being subjected to a vacuum from both sides, maintains a horizontal position (pos. A FIG. 7) and thus the relative extremity of the hole (16a of 16) is left free; in other words the pneumatic valve remains open, (10).

Hence as a result of the foregoing procedures each tube (11) communicates with the collector (2) and thus can induce suction.

When replacing a tube on the console the relative shaft (23) whose foremost extremity protrudes from the central area of the forked housing, is pushed inwards causing the corresponding shut-off valve to be opened, (21). The corresponding chamber (19) is now reduced to normal atmospheric pressure as it communicates with the outside through the small hole (30); it should be noted here that the narrow bore in this section of the channel (29) does not allow the creation of a vacuum in the chamber (19) other than minimally, when the valve (21) is opened.

The diaphragm (18), whose upper side is subjected to a pressure greater than that to its lower, inflects (pos. B FIG. 7) by dint of its convex nature and closes the aperture (16) thus breaking communication between the collector (2) and the corresponding tube.

The increased thickness of the sealing surface (18b) enables it to maintain a flat profile, essential to the tight sealing of the pneumatic valve.

Hence, when a tube is replaced there will be seen to be no suction within that tube while suction continues in the other tube as, even though the switch relative to the replaced tube becomes engaged—therefore open—the operation of the suction pump remains uninterrupted.

When both tubes are replaced on the console the buttons of both switches (33) are pressed in, thus the operation of the suction pump is arrested.

Subsequently, the withdrawal of one or both of the tubes from the console will cause suction to recommence in the manner described above.

In the second embodiment of the console, when both tubes are replaced in the cover's forked housings the switches' (33) buttons are all engaged, thus the first solenoid valves cause the suction pump to arrest. When both tubes are withdrawn from the forked housings the switches' (33) buttons are not engaged, thus the first solenoid valves cause the (re) starting of the suction pump thereby creating a vacuum in the collector (2); in this event the buttons of the switches (53) are also disengaged; hence the second solenoid valves (50) place the chamber (19) in communication with the collector (2) in the manner described above; in this manner the diaphragm (18), which is subjected to a vacuum from both sides, maintains a horizontal position (pos. A ) and the relative extremity of the hole is left free, (16a of 16); in other words the pneumatic valve (10) remains open and the relative tube (11) is placed in communication with the collector so producing suction.

When a tube is replaced in its respective forked housing the corresponding shaft is pushed inwards and, engaging the button (53a) of the second switch (53) causes the corresponding second solenoid valve (50) to operate, which valve places the chamber (19) in communication with the outside; in this manner the diaphragm (18), whose upper side is subjected to a pressure greater than that to its lower, inflects (pos. B) by dint of its convex nature and closes the aperture (16) thus breaking communication between the collector (2) and the corresponding tube.

Hence, when a tube is replaced there will be seen to be no suction within that tube while suction continues in the other tube, for even though the switch corresponding to the replaced tube becomes engaged, the operation of the suction pump remains uninterrupted.

While the dentist is working he may move the cover (38) at the same time arranging it to his own convenience; this is due to the particular type of attachment between the cover and the box-like shell which, it will be remembered, is fixed to the dentist's main assembly.

In the event that the articulated attachment should comprise a greater number of arms (57) the dentist may, on terminating treatment turn the arms so as to arrange them one above the/another; in this manner the console becomes notably less of an encumbrance when not in use.

The special structure in both embodiments allows the console's cleaning and maintenance to be remarkably simple. All of that which the tube sucks in enters by way of the holes (16) into the filter (4) as these holes give out into the collector by way of the open plane of the filter. The fluids having passed through the perforated walls of the filter drawer, are evacuated through the manifold (8a)—or manifold (8b)—and thence through the hose (8) whereas the solid bodies remain inside the filter (4). For cleaning of the filter one need only unscrew the stopper (3), grasp the handle (4a), and withdraw the filter which may then be emptied and subsequently washed; this operation may be carried out without the soiled parts of the filter coming into contact with the operator's hands. For checking and maintenance of an exceptional nature, such as the changing of a diaphragm or switch etc. one simply removes the cover (38)—in the event that this is attached direct to the box-like shell—in order to gain access to the compartment (13) wherein are located all those parts which are subject to breakdown, or which need regular checking and cleaning.

Obviously numerous modifications of a practical nature may be made to the constructional details of the invention without there being in any way a deviation from the frame—work of protection afforded to the conceptual ideas behind the invention as claimed below.

What is claimed is:

1. A console specifically designed for the suction tubes of suction units of the kind used in dentistry of a type having one or more housing(s) for tube(s) comprising pneumatic devices for arresting the suction within a tube when the latter is replaced on the console, electrical devices for arresting the operation of the suction pump when all the tubes are replaced on the console, and filtering means for effecting a first stage filtering of the spittle and the like sucked into the tube, comprising a box-like shell furnished with a longitudinally disposed collector accessible from without at one of its lateral extremities, closed by a removable stopper, inside which collector is positioned a filter drawer with an open top and furnished with perforated walls whose shape and dimensions are such that it occupies substantially all of the internal space inside said collector, said collector being connected to the suction pump by means of a first hose and, by the interpositioning of a pneumatic valve, to each of the said tubes by means of second hoses each of which are connected to a duct located in said box-like shell, which gives out into the collector and correspondingly into the open top of the filter drawer, said box-like shell also comprising an upper compartment with an open top serving to accommodate the said pneumatic devices and the command components of said electrical devices; a cover, in which are located forked housings into which the tubes are placed, which can be attached to the top of the said box-like shell thereby making it secure; and checking means for determining a sole correct position of the filter drawer for its introduction into said collector, said checking means comprising a pair of upper guide rails located on the internal upper surface of said collector and running in a longitudinal direction parallel with each other at a reciprocal distance slightly greater than the width of the open top of the filter drawer; a pair of lower guide rails located on the lower internal surface of the said collector running in a longitudinal direction and parallel with each other at a reciprocal distance which is less than the width of said filter's open top, provision having been made on the wall of the filter opposite to its open top for a pair of corresponding elements inclined downwards and running longitudinally and parallel with each other at a reciprocal distance which is slightly greater than that distance existing between the outer surfaces of the lower guide rails; and the distance between the said pairs of lower and upper guide rails being less than the width of the open top of the said filter.

2. Console according to claim 1, wherein said console comprises in the compartment, for each respective tube, a cavity with open top into the bottom of which gives out the extremity of a first conduit located in the box-like shell, to which extremity is connected said second hose, said cavity further comprises a through hole which communicates with said collector and which gives out into said cavity at a height above the hole in the cavity itself and slightly below the rim of said cavity; said first conduit and said through hole forming part of said duct.

3. Console according to claim 2, wherein relative to each cavity, a diaphragm which constitutes the choke of the pneumatic valve, positioned above said cavity in such a way that it covers the cavity completely, said diaphragm presenting a convex aspect to the hole when its perimeter is seated and defining within its own area a sealing surface whose action is to cover said hole completely; and the area of said sealing surface being of a thickness greater than the remaining area of said diaphragm.

4. Console according to any one of the preceding claims wherein, relative to each cavity, a covering element having an outer perimeter which completely surmounts the said diaphragm, attached to said box-like shell and serving to establish above said diaphragm, a chamber, placed in communication with said collector by way of a second conduit located partly in said box-like shell and partly in the covering element; said covering element further containing a small hole one of whose extremities gives out into said chamber and whose other extremity is placed, by means of a shut-off valve commanded by said tube and furnished with a sliding shaft running through the body of the valve and protruding from both its extremities, in communication with the outside, or closed, according to whether the tube is replaced on, or withdrawn from, said console.

5. Console according to claim 4 wherein said covering element comprises on its upper side supporting posts which serve to accomodate a switch that constitutes said command element for the electrical devices; said posts being positioned in close proximity to the rear extremity of said shaft (23) in order that said switch may be commanded by said rear extremity.

6. Console according to claim 1, wherein said cover is fixed to said box-like shell in order to cover said compartment and comprises, at a point corresponding to the center of the forked housing a through hole which allows the foremost extremity of said shaft of the shut-off valve to protrude from said cover.

7. Console according to claim 1, and second solenoid valves, one for each tube respectively, located on said box-like shell and serving to open or close said pneumatic valves; second electrical switches, one for each tube respectively, contained in said cover and caused to function by the tube itself by the interpositioning of a sliding shaft, said second electrical switches being wired to said second solenoid valves; and articulating devices serving to attach said cover to said box-like shell.

8. Console according to claim 7 wherein said articulating devices comprise: a first socket incorporated into the box-like shell; a first pin incorporated into said cover; and at least one arm furnished at one of its extremities with a second socket whose dimensions are such that it may receive said first pin and at its other extremity with a second pin whose dimensions are such that it may be inserted into the first socket.

9. Console according to claim 8 wherein the underside of said arm offers a longitudinally disposed groove enclosed with a covering element save at its extremities.

* * * * *